United States Patent [19]

Schröder

[11] Patent Number: 4,713,249
[45] Date of Patent: Dec. 15, 1987

[54] CRYSTALLIZED CARBOHYDRATE MATRIX FOR BIOLOGICALLY ACTIVE SUBSTANCES, A PROCESS OF PREPARING SAID MATRIX, AND THE USE THEREOF

[76] Inventor: Ulf Schröder, Fagottgränden 11 B, S-223 68 Lund, Sweden

[21] Appl. No.: 789,933

[22] PCT Filed: Jul. 4, 1983

[86] PCT. No.: PCT/SE83/00268

§ 371 Date: Feb. 22, 1984

§ 102(e) Date: Feb. 22, 1984

[87] PCT Pub. No.: WO84/00293

PCT Pub. Date: Feb. 2, 1984

[22] Filed: Oct. 22, 1985

Related U.S. Application Data

[63] Continuation of Ser. No. 588,099, Feb. 22, 1984, abandoned.

[30] Foreign Application Priority Data

Nov. 12, 1981 [SE] Sweden ............................ 8106723
Jul. 9, 1982 [SE] Sweden ............................ 8204244

[51] Int. Cl.⁴ .......................... A61K 9/26; B01J 13/02
[52] U.S. Cl. ................................ 424/488; 424/1.1; 424/484; 427/213.3; 428/402.24
[58] Field of Search ............... 427/213.3; 428/402.24; 424/22, 35, 484, 488

[56] References Cited

U.S. PATENT DOCUMENTS

| | | | |
|---|---|---|---|
| 3,185,625 | 5/1965 | Brown | 424/22 X |
| 3,558,507 | 1/1971 | Harbort | 264/4.1 |
| 3,658,678 | 9/1973 | Lindsay et al. | 424/1 |
| 3,663,685 | 5/1972 | Evans | 424/1 |
| 3,663,686 | 5/1972 | Grotenhuiz et al. | 424/1 |
| 3,663,687 | 5/1972 | Evans | 424/1 |
| 3,786,123 | 2/1974 | Katzen | 424/35 X |
| 4,118,336 | 10/1978 | Morishita et al. | 428/402.24 X |
| 4,501,726 | 2/1985 | Schröder et al. | 424/1.1 |

FOREIGN PATENT DOCUMENTS 6904024 12/1974 Sweden.
7800005 12/1978 Sweden.
795977 6/1958 United Kingdom .................. 424/37

OTHER PUBLICATIONS

Radley, J. A.; Starch and Its Derivatives, 4th Ed., Chapter 6, pp. 194–202, Chapman and Hall Ltd., London (1968).

*Primary Examiner*—Richard D. Lovering
*Attorney, Agent, or Firm*—Merchant, Gould, Smith, Edell, Welter & Schmidt

[57] ABSTRACT

The invention shows that it is possible to produce a depot matrix for biologically active substances, consisting of carbohydrate microspheres, such that the carbohydrate polymers included in the microsphere are stabilized to a microsphere by crystallization, which implies using non-covalent bonds, the substance enclosed retaining its biological activity.

12 Claims, No Drawings

CRYSTALLIZED CARBOHYDRATE MATRIX FOR BIOLOGICALLY ACTIVE SUBSTANCES, A PROCESS OF PREPARING SAID MATRIX, AND THE USE THEREOF

This application is a continuation of Ser. No. 588,099, filed Feb. 22, 1984 and now abandoned. This application also contains subject matter common to Ser. No. 522,159, filed July 8, 1983, now U.S. Pat. No. 4,501,726, based on PCT application Ser. No. SE 82/00381, filed Nov. 12, 1982 and claiming priority from Swedish application Ser. No. 8106723-3, filed Nov. 21, 1981.

BACKGROUND

Biologically active substances supplied to an organism are, in most cases, rapidly digested by the organism. In view hereof, the supply of substances must be repeated at regular intervals in order to establish a therapeutically active concentration within the organism. Such supply of biologically active substances to organisms is important int. al. in the fields of human and veterinary medicine, or in controlling different types of infestants (such as insects, fungi etc.) in agriculture and forestry.

In order to avoid the disadvantages of repeated administration, it is endeavoured to find matrices which, together with the substance, provide a depot effect, by which is meant that the substance in one way or another is adsorbed, coupled to or enclosed in a matrix from which it is then released, via different mechanisms, during a prolonged period of time. The great advantage of this type of administration is that the substance is supplied to the organism at a uniform rate; the peaks and valleys in concentration encountered with normal administration are avoided. By biologically active preparations are meant such preparations or substances as are capable of affecting organisms. Examples of such preparations are therapeutically active preparations, insecticides or herbicides, enzymes, antibodies, antigens, allergens, hormones, live or killed and whole or decomposed microorganisms or virus. As practical examples of the fields of use of the present invention, mention may be made of 1. Insulin: Patients suffering from diabetes must inject insulin at regular intervals or during meals in order to maintain the blood sugar content at an acceptable level. Great advantages would be obtainable if a depot preparation of insulin could be administered in a simple manner, implying that the injection frequency could be reduced considerably;

2. Vaccination: For the vaccination of humans, adjuvants cannot be used. However, it has been shown in literature that the immunogenic response will be far better if the body is subjected to long-time exposure of the antigen. For vaccination purposes, it is important that the depot matrix is not itself immunogenic, and that it can be excreted from the body. For example, vaccination tests conducted on human beings against bee allergens have shown that these allergens, dissolved in water and injected subcutaneously, are excreted within 4 hours.

The production of depot matrices for different types of preparations is well-documented in literature, and some preparations are also commercially available.

The invention described in the present application uses polymers as depot matrix. Different types of polymers are described in literature. (Chem. Eng. Commun. (1980) 6, 1–48 or Int. J. Pharm. (1980) 7, 1–18). Among the desirable properties of such a polymer preparation are the following:

1. The polymer should in itself be chemically inert in biological systems.
2. The polymer should be biologically well-characterised.
3. The polymer should be non-toxic and non-immunogenic.
4. The polymer should be excretable from the body via normal routes.
5. The polymer preparation should be readily administrable.
6. The polymer preparation should be capable of releasing a biologically active substance, and the release rate of the active substance should be readily controllable.
7. The polymer preparation should be able to enclose and release substances of different molecular weights.

Existing polymer systems described in the above-mentioned summary reviews are all of the type covalently cross-linked polymers in which the covalent cross-linkage in some cases is unstable in biological systems, and in which the biologically active substance is covalently bonded to the polymer. This instability causes degradation of the polymer preparation, whereby the preparations are released.

A different type of release is obtained if crystalline substances (such as crystallised proteins) are enclosed in the covalently cross-linked polymer preparation. By utilising a varying degree of porosity in the polymer preparation, varying release times are obtained.

In general it may be said that it is endeavoured, in developing polymer preparations for administration of biologically active substances, to use polymers which are as "pure" as possible. One such "pure" polymer class is represented by the carbohydrates. Presentday methods of preparing carbohydrate matrices comprise a covalent coupling of the polymer chains included (GB Pat. No. 924054) or heat treatment (SE Pat. No. 4024/69) in order to obtain stable matrices.

DESCRIPTION OF THE INVENTION

The invention is based upon a novel technique for stabilising carbohydrate polymers according to the appended claims. This technique involves emulsifying a solution of the polymer in a hydrophobic emulsifying medium, whereby spherical droplets of the soluble carbohydrate polymer are obtained in the emulsifying medium. To stabilise the sphere, the said emulsion is then poured into a liquid capable of crystallising the carbohydrate polymer to a complex relatively insoluble in water.

Crystallisation implies that the type of bonds holding the carbohydrate polymers together in a microsphere is chemically characterised as non-covalent of the type hydrogen bonds, ion bonds or van der Waals forces, the majority consisting of hydrogen bonds.

The resulting polymer matrix has such characteristics that it can retain biologically active substances in the non-covalently cross-linked polymeric lattice, the biologically active substance being released concurrently with the slow redissolution of the crystallised carbohydrate matrix.

The simplest way of incorporating the biologically active substance is to admix it to the dissolved carbohydrate polymer before this is mixed with the emulsifying medium.

The matrix material in the production of these spheres or particles consists of carbohydrate polymers. The technique described in the present invention makes it possible to use the carbohydrates dextran, pullullan, glucogen, starch, agarose, cellulose, alginate, chitosan or carrageenan, and different derivatives thereof.

In some cases, also the carbohydrate per se may be of interest as a biologically active substance. One example hereof is the carbohydrate heparin which is used therapeutically as an anticoagulant.

As regards the molecular weight of the carbohydrates, the technique has been shown to function within a very large range. For instance, crystallised carbohydrate spheres have been produced from glucose, sucrose and maltose. Dextrans and dextrins having an average molecular weight from about 800 up to several millions have also been shown to function. The upper limit of the molecular weight in the preparation of crystallised carbohydrate spheres according to the present invention is limited only by the solubility of the respective carbohydrates in their solvents.

The modification of these carbohydrate polymers to different types of derivatives can be carried out in such a manner that the ability of the carbohydrates to adsorb for example hydrophobic or charged substances, is changed. Examples of well-documented hydrophobic substituents are cholesterol, DEAE, or Ciba chrome blue which all can be covalently coupled in simple manner to the carbohydrate polymer. Correspondingly, charged groups of the type $-SO_4$ or $-NH_2$ can be covalently coupled to the carbohydrate matrix for adsorption of charged substances. The above-mentioned substituents are commercially available, coupled to the carbohydrate polymer dextran, from Pharmacia AB at Uppsala.

Of the above-mentioned carbohydrate polymers, the polymers dextran, starch, glucogen, or pullullan are preferred on grounds previously described (see points 1-7, on pp. 2-3). The main reason is that these polymers are extremely well characterised in biological systems. Of the above-mentioned polymers, however, dextran must be put in the first place as an example of a non-enzymatically (in tissue) degradable matrix for biologically active substances. Where starch, glucogen or pullullan is concerned, the alpha-amylase concentration determines the time of degradation and thus also the release time of the biologically active substances. In the case of dextran, it is only the physical parameters, such as the pH or ionic strength, which redissolve the crystallised matrix and thus control the release.

The disadvantage of an enzymatically controlled release is that, in the case of for example alpha-amylase, the concentration thereof may vary within large ranges in body fluids for different diseases. In other cases, the enzyme concentrations may vary between patients or in the same patient at different times of the day and thus affect the release time of the biologically active substance.

The present invention describes how one prepares crystallised carbohydrate spheres with enclosed biologically active substances. The method is characterised in that the carbohydrate polymer is dissolved in a solvent having a high dielectric constant to a concentration lying within the range 0.1-200% (weight/volume). By high dielectric constant is here meant a solvent or combinations of solvents having a dielectricity constant of more than about 35. Useful such solvents are, inter alia, dimethyl formamide, ethylene glycol, dimethyl sulphoxide, water and formamide, or mixtures thereof. The biologically active substance is added to this solution. The resulting mixture of dissolved carbohydrate polymer and biologically active substance is then emulsified in an emulsion system comprising the said solution and an emulsion medium consisting of a liquid which is immiscible with said solution and which has the further characteristic of contributing to the formation of droplets of the carbohydrate solution in the emulsion medium.

As examples of useful emulsion media mention may be made of vegetable oils, preferably rapeseed or maize oil. Other useful hydrophobic emulsion media include paraffin oils or silicone oils. Another type of emulsion medium includes organic solvents in which one or more emulsifiers have been dissolved. Useful such organic solvents include, inter alia, xylene, toluene, ethyl benzene, diethyl benzene, propyl benzene, ethylene chloride and other similar solvents, as well as mixtures thereof.

The technique of using emulsion media in combination with different emulsifiers in order to obtain varying diameters in the preparation of microspheres is well documented in literature and will not be described in detail in the present context.

To emulsify the emulsion, use is made of a sonicator or high-pressure homogeniser. The resulting emulsion in which the carbohydrate solution is emulsified in the form of droplets, is stabilized by transferring it to a liquid capable of crystallising the carbohydrate polymer, whereby the biologically active substance is enclosed. Useful such liquids are ethanol, methanol or acetone, although the latter is preferred. After crystallisation, the resulting matrix is further washed with acetone, whereupon drying is effected simplest by rotational evaporation or in a warming cupboard.

It is important that the enclosed substances retain their biological activity also after release from the matrix.

In this respect, the present invention shows that hormonal proteins of the type insulin and interferon, enzymes such as plasmin and beta-galactosidase as well as monoclonal antibodies retain their biological activity after enclosure and subsequent release from the matrix.

In some cases, it is not possible to enclose substances within the matrix. One then has the possibility of covalently coupling the substance to the matrix, in which case it is important that the technique of covalent coupling does not imply any appreciable degree of cross-linking of the matrix because such cross-linking would completely annihilate the release mechanisms upon dissolution of the carbohydrate matrix, as has previously been discussed.

Such a type of covalent coupling is obtained if use is made of tresyl chloride as the activating substance because this coupling technique does not result in cross-linking of the carbohydrate matrix (Biochem. Biophys. Res. Comm. (1981) 102, 449-457).

The following Examples are not to be regarded as restrictive, but rather as illustrative of the main features of this invention.

EXAMPLE 1

1 gram of a 50% (weight/volume) aqueous solution of dextran, having a molecular weight of 40,000, was mixed with 100 μl of an ovalbumin solution containing 100 mg of ovalbumin/ml of water. 5 μl of 125-I-labeled ovalbumin had previously been added to the latter solution.

The dextran-ovalbumin solution was suspended in 25 ml of vegetable oil in a 100 ml beaker and cooled to +4° C. The mixture was emulsified by ultrasonics for 1 minute, whereupon the emulsion was poured into 200 ml of acetone in which the emulsifier Tween 80 had been dissolved to a concentration of 0.1% (weight/volume). While the emulsion was being carefully poured into the acetone solution, it was stirred at about 1,000 rpm. The resulting dextran spheres which had been stabilised by crystallisation and contained ovalbumin enclosed therein were washed 4 times more with the said acetone solution, whereupon they were air-dried.

Normally, such a test gives a recovery of about 250 mg of spheres in which 60–70% of ovalbumin added have been enclosed in the carbohydrate matrix. The size of the spheres prepared by this technique lies between 0.01 and 10 μm. By varying the composition of the emulsion medium, spheres having a diameter of up to 1 mm are readily produced.

EXAMPLE 2

The same as in Example 1, but with the difference that the dextran was crystallised in methanol or ethanol, instead of acetone.

EXAMPLE 3

The same as in Example 1, but with the difference that 0.2 g of starch was dissolved in water, and that the starch solution was emulsified in toluene containing the emulsifier Gafac PE-510 (5% weight/volume), instead of dextran and oil.

EXAMPLE 4

The same as in Example 1, but with the difference that 1 g of 0.2% agarose or carageenan at a temperature of +40° C. was used instead of dextran.

EXAMPLE 5

The same as in Example 1, but with the difference that 1 g alginate was used instead of dextran and emulsified by means of a 0.1% admixture of the emulsifier Gafac RM-410 into the oil instead of pure oil.

EXAMPLE 6

The same as in Example 1, but with the difference that 1 g of 1% chitosan dissolved at pH 5 was used instead of dextran.

EXAMPLE 7

The same as in Example 1, but with the difference that 3 g of cellulose were dissolved in 150 g of N-ethyl pyridine chloride and 75 g of dimethyl formamide, 1 g of this solution being used instead of dextran.

EXAMPLE 8

The same as in Example 1, but with the difference that a 200% (weight/volume) aqueous solution of sucrose was used instead of dextran.

EXAMPLE 9

The same as in Example 1, but with the difference that a 30% (weight/volume) aqueous solution of glycogen was used instead of dextran.

EXAMPLE 10

The same as in Example 1, but with the difference that ovalbumin was not used, and that the per se biologically active carbohydrate polymer heparin was dissolved to a concentration of 50% (weight/volume) in water and used instead of dextran for the production of crystallised spheres.

EXAMPLE 11

100 mg of dried spheres according to Example 1 were slurried in 10 ml of PBS at pH 7.2. At different times it was investigated how much of the enclosed ovalbumin had been released from the spheres by filtrating the mixture through a filter having a molecular "cut-off" of 100,000.

With the above-mentioned spheres, a half-life of released ovalbumin of about 12 days is obtained.

By varying the concentration or the molecular weight of the dextran polymer, the half-lives can be varied in simple manner. By increasing the concentration or using a higher molecular weight of the polymer, a longer half-life is obtained.

EXAMPLE 12

As in Example 1, it is possible to use substituted dextrans in the production of the spheres. To investigate the documented adjuvant effect of DEAE and $SO_4$-substituted dextrans, these were mixed with unsubstituted dextran at the ratios 0%, 33%, 66% and 100%. Such spheres with enclosed ovalbumin were then injected subcutaneously in mice, whereupon IgG and IgM antibodies against ovalbumin were determined by means of a so-called microtiter-ELISA-method.

It proved that the immunological response was directly correlated to the amount of adjuvant, and that the antibody titer of the mice that were given ovalbumin in unsubstituted dextran spheres was significantly higher as compared with the mice injected with the ovalbumin merely dissolved in water.

EXAMPLE 13

To investigate whether a biologically active protein retains its activity, insulin was enclosed in dextran spheres made from a 20% (weight/volume) dextran solution. The biological activity was then evaluated in that the insulin released from the spheres was shown to retain its capacity for in vitro stimulation of fat cells to produce fatty acids. At a release test conducted on enclosed insulin, tested in the same manner as in Example 2, but with 125-I insulin, there was obtained from spheres prepared from a 35% solution of dextran having a molecular weight of 500,000, a half-life of about 6 days.

EXAMPLE 14

As in Example 10, interferon was enclosed in dextran spheres, whereupon the antiviral effect of the interferon was determined in a so-called plaque-assay.

About 35% of the antiviral effect of the interferon supplied could be detected.

EXAMPLE 15

As in Example 10, the enzyme plasmin was enclosed in dextran spheres, whereupon its enzymatic activity was determined by means of the substrate H-D-Val-Leu-Lys-pNA after release from the spheres. The dried spheres contained about 1% of plasmin with a recovery of the biological activity of about 75%.

EXAMPLE 16

As in Example 10, the enzyme beta-galactosidase was enclosed in dextran spheres, whereupon the enzymatic activity was determined after release from the matrix by means of the substrate ONPG.

The dried spheres contained about 5% of the enzyme with a recovery of biological activity of 70%.

EXAMPLE 17

As in Example 10, a monoclonal antibody directed against the protein PHA was enclosed in the spheres, whereupon its binding activity was determined in a so-called sandwich-ELISA after release from the matrix. Recovery of the biological activity was 65%.

EXAMPLE 18

As in Example 10, 125-I labeled biosynthetic growth hormone was enclosed, although in this instance an 80% solution of a dextrin (Awedex W90, Stadex AB, Malmö) was employed.

Recovery of radioactivity was 100%.

EXAMPLE 19

A 200% (weight/volume) solution of maltose was prepared, whereupon the pharmaceuticals metotrexate and vincristine ($^3$H-labeled), respectively, were enclosed in spheres by the same technique as in Example 1.

Recovery of metotrexate was 82% and for vincristine 22%.

EXAMPLE 20

As in Example 19, metotrexate and vincristine were enclosed in the carbohydrates dextran T1 and glucose.

Recovery for metotrexate was for both carbohydrates 65%, and for vincristine a recovery of 40% was obtained.

EXAMPLE 21

As in Example 1, spheres were produced, but with the difference that 1 g of 30% (weight/volume) dextran T500 was used as carbohydrate, and that 250 μl of albumin (100 mg/ml) were added fo r enclosure.

In this manner, 65% of added protein were enclosed, which corresponds to 40% of the dry weight of the spheres.

EXAMPLE 22

In present day treatment of bee allergies on human beings, successively higher doses of an aqueous solution of the allergen are injected.

To test whether the immunological response is changed if a depot preparation of be allergens is used, bee allergen was enclosed in dextran spheres according to Example 1 and injected subcutaneously in mice whereupon the immunological response with respect to IgG was determined at different times. For comparison, bee allergen and pure water and bee allergen suspended in Freund's complete adjuvant were injected. The antibody content in the group that had been given bee allergen dissolved in water, showed a slight rise after 1 week and then receded to undetectable contents. On comparing the depot preparation to Freund's adjuvant, it was found that the antibody content rose more quickly when the bee allergens were enclosed in the depot matrix. After 10 weeks, the IgG contents in serum were still rising for both groups, which shows that rhe depot preparation is highly efficient when it is desired to obtain high contents of antibodies.

EXAMPLE 23

1 gram of aqueous solution of dextran having a molecular weight of 10,000 was mixed with 50 μl of the low-molecular pharmaceutical metotrexate. The total amount added was 5 mg which, besides, was 3-H-labeled. The mixture was processed according to Example 1 and the result was that 92% of metrotrexate added were enclosed in the dried spheres.

EXAMPLE 24

To investigate the release from a matrix degradable by enzymes, the following test was carried out.

100 mg of spheres produced from starch dissolved in formamide according to Example 1, were activated with tresyl chloride, whereupon 125-I myoglobin was coupled to the spheres. After careful washing to remove adsorbed myoglobin, alpha-amylase was added in a concentration that was 100 times higher than in normal human serum. Within two hours, about 25% of coupled myoglobin had been released from the matrix. By further increasing the amount of alpha-amylase 10 times during the next 24 hours, a total release of about 45% of coupled myoglobin was obtained. During the last 24 hours, the alpha-amylase concentration in the test was about 20,000 times higher than in normal human serum.

I claim:

1. A composition useful for the prolonged release of a biologically-active substance comprising a sphere or particle comprising a non-covalently cross-linked crystalline polymeric carbohydrate matrix, said matrix incorporating 0.001–50% by weight of an absorbed or covalently bonded biologically-active substance.

2. The composition of claim 1 wherein said sphere or particle has an average diameter within the range of 0.01–1,000 μm.

3. The composition of claim 1 wherein said sphere or particle has an average diameter within the range of 0.01–1.0 μm.

4. The composition of claim 1 wherein said carbohydrate is selected from the group consisting of dextran, starch and the derivatives thereof.

5. The composition of claim 1 wherein the carbohydrate is selected from the group consisting of alginate, chitosan, agarose, carrageenan, cellulose, glycogen, pullullan and the derivatives thereof.

6. The composition of claim 1 wherein said biologically-active substance is an antigen.

7. The composition of claim 1 wherein the biologically-active substance is insulin.

8. The composition of claim 1 wherein the biologically-active substance is an allergen.

9. The composition of claim 1 wherein the biologically-active substance is a growth hormone.

10. A process for producing a composition useful for the prolonged release of a biologically-active substance, comprising,
(a) forming a solution of a polymeric carbohydrate and a biologically-active substance in one or more hydrophillic solvents;
(b) emulsifying the mixture of the carbohydrate and the biologically active substance in a liquid hydrophobic medium to form spherical droplets; and (c) introducing the emulsion into a crystallizing medium to form spheres having a non-covalently cross-linked crystalline polymeric carbohydrate matrix, said matrix incorporating 0.001–50% by weight of the biologically-active substance.

11. The process of claim 10 wherein the droplets are crystallized by introducing them into a crystallizing medium comprising acetone, ethanol or methanol.

12. The process of claim 10 wherein the emulsification is conducted at 4°–40° C. so that the activity of the biologically-active substance is preserved.

* * * * *